US00PP28994P3

(12) United States Plant Patent
Kallsen et al.

(10) Patent No.: US PP28,994 P3
(45) Date of Patent: Feb. 27, 2018

(54) MALE PISTACHIO TREE NAMED 'FAMOSO'

(50) Latin Name: ***Pistacia vera* L.**
Varietal Denomination: Famoso

(71) Applicant: The Regents of the University of California, Oakland, CA (US)

(72) Inventors: Craig E. Kallsen, Davis, CA (US); Dan E. Parfitt, Davis, CA (US); Joseph Maranto, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/999,156

(22) Filed: Apr. 4, 2016

(65) Prior Publication Data

US 2016/0309631 P1 Oct. 20, 2016

Related U.S. Application Data

(60) Provisional application No. 62/147,540, filed on Apr. 14, 2015.

(51) Int. Cl.
*A01H 5/02* (2006.01)

(52) U.S. Cl.
USPC ..... Plt./152

(58) Field of Classification Search
USPC ..... Plt./152
See application file for complete search history.

(56) References Cited

PUBLICATIONS

Hickey (1973). "Classification of the Architecture of Dicotyledonous Leaves," American Journal of Botany, 60(1): 17-33.
The Jul. 1, 2002 Test Agreement for Trees (No. 2003-5006) between Tejon Ranch and The Regents of The University of California, 9 pages.
The Jul. 1, 2002 Test Agreement for Trees (No. 2003-5066) between Pioneer Nursery (Little Creek) and The Regents of The University of California, 9 pages.
The Jun. 1, 2014 Test Agreement for Trees (No. 2014-5013) between Mojave Pistachios, LLC and The Regents of The University of California, 7 pages.
The Jun. 1, 2014 Test Agreement for Trees and Rootstocks (No. 2014_5014) between Paramount Farming Company, LLC and The Regents of The University of California, 7 pages.
The Aug. 1, 2014 Test Agreement for Trees (No. 2014-5016) between Saeed, LLC and The Regents of The University of California, 7 pages.

*Primary Examiner* — Susan McCormick Ewoldt
(74) *Attorney, Agent, or Firm* — Morrison & Foerster LLP

(57) ABSTRACT

A new male pistachio tree (*Pistacia vera* L.) designated as 'Famoso', particularly characterized by mid- to late-season flowering time, is provided. The male pistachio tree 'Famoso' is further characterized by consistent flowering from year to year, and production of a large amount of pollen over an extended period. In addition, 'Famoso' is characterized by precocious flowering three to four years after budding.

10 Drawing Sheets

CROSS-REFERENCE TO RELATED APPLICATION

This application claims the benefit of U.S. Provisional Application No. 62/147,540, filed Apr. 14, 2015, which is incorporated herein by reference in its entirety.

Latin name: Botanical/commercial classification: *Pistacia vera* L.

Varietal denomination: The varietal denomination of the claimed pistachio variety is 'Famoso'.

BACKGROUND OF THE INVENTION

An objective of pistachio breeding programs is to develop improved male pollinators of the female pistachio variety 'Kerman' (not patented). The female pistachio variety 'Kerman' is the main later-season pistachio cultivar grown in California and in other parts of the world. The male pistachio variety 'Peters' (not patented) is a common male cultivar used as a pollen source to pollinate 'Kerman'. Although 'Peters' is viewed as the industry standard pollinator variety for 'Kerman', 'Peters' often flowers later than 'Kerman' and has a history of providing poor flowering overlap with 'Kerman'. This poor flowering overlap is especially seen during years with insufficient chilling. Even in seasons of sufficient chilling, 'Peters' is not very precocious, meaning that 'Peters' is slow to produce flowers as a juvenile tree. This is particularly apparent when 'Peters' is compared to female 'Kerman' trees, which will have many flowers at $6^{th}$ or $7^{th}$ leaf, while 'Peters' trees will have either none or relatively few. Typically, the female variety 'Kerman' is approximately one year ahead of the male variety 'Peters' in terms of flower development, which results in a year of lost production. Further, in low chill years, 'Peters' has performed very poorly. In some young orchards, 'Peters' produced almost no flowers, the flowers that were produced had no pollen, and 'Peters' often bloomed 1-2 weeks later than 'Kerman'. Over time, the use of 'Peters' has resulted in inadequate pollination of 'Kerman' and reduced yield potential.

Pistachio growers are in need of a male pistachio variety that is more precocious than 'Peters', performs better in low chill years, and has a better flowering overlap with the female variety 'Kerman'. Thus, there exists a need for improved pollinator varieties, such as male varieties having improved flowering overlap with 'Kerman'. The present male pistachio variety 'Famoso' described herein is a product of the breeding efforts to produce improved male pistachio varieties.

SUMMARY OF THE INVENTION

The present invention relates to a new and distinct pistachio cultivar (*Pistacia vera* L.) that has been denominated as 'Famoso', and more particularly as a male pistachio variety that has a better overlap with the flowering period of the female pistachio variety 'Kerman' than does the male pistachio variety 'Peters'. In addition, the male pistachio variety 'Famoso' is more precocious than 'Peters'; 'Famoso' produces flowers three to four years after budding as compared to 'Peters', which typically takes four to five years to produce flowers after budding. The male pistachio variety 'Famoso' also has a more consistent flowering period that is more coincident with the flowering period of the female pistachio variety 'Kerman'. In contrast, the male pistachio variety 'Peters' has poor flowering overlap with 'Kerman' as well as poor blooms during some years. 'Peters' has especially poor blooms during years with low chilling, which are expected to become more frequent in future years in view of the warming climate.

By providing a better overlap in flowering period with 'Kerman' than is provided by 'Peters', 'Famoso' may improve 'Kerman' yield, especially in years when 'Peters' flowers significantly later than 'Kerman'. 'Famoso' flowering is more consistent than 'Peters', and 'Famoso' also produces a large amount of pollen over an extended period. 'Famoso' is potentially significant as an alternative to 'Peters' for the Californian, New Mexican, Arizonan, and world-wide pistachio industries. 'Famoso' may be used as the pollinizer for other mid- to late-season pistachio cultivars such as 'Kerman'. 'Famoso' may also be used as an additional pollinizer of mid- to late-season female pistachio varieties (e.g. 'Kerman') in orchards along with the male variety 'Peters' or other male pistachio varieties.

The cross that produced 'Famoso' was originally made during Year 1, and the original seedling of 'Famoso' was planted at a research plot near Bakersfield, Calif., USA during Year 2. The cross was made between *Pistacia vera* L. female '2-35' (not patented) and *Pistacia vera* L. male 'ES#4' (not patented). 'Famoso' was originally designated as selection 'B19-69'. 'B19-69' was budded (asexually propagated via T-buds) onto rootstocks at two test locations called Tejon Ranch and Little Creek in eastern Kern County, Calif., USA. Buds from the original 'B19-69' tree were budded onto 'UCB-1' (not patented) rootstocks at both test locations in Year 13. Selection 'B19-69' was chosen as a candidate for release under the variety name 'Famoso'. The variety 'Famoso' has been found to be stable and reproduce true to type through successive asexual propagations.

BOTANICAL DESCRIPTION OF THE PLANT

Figure 1:
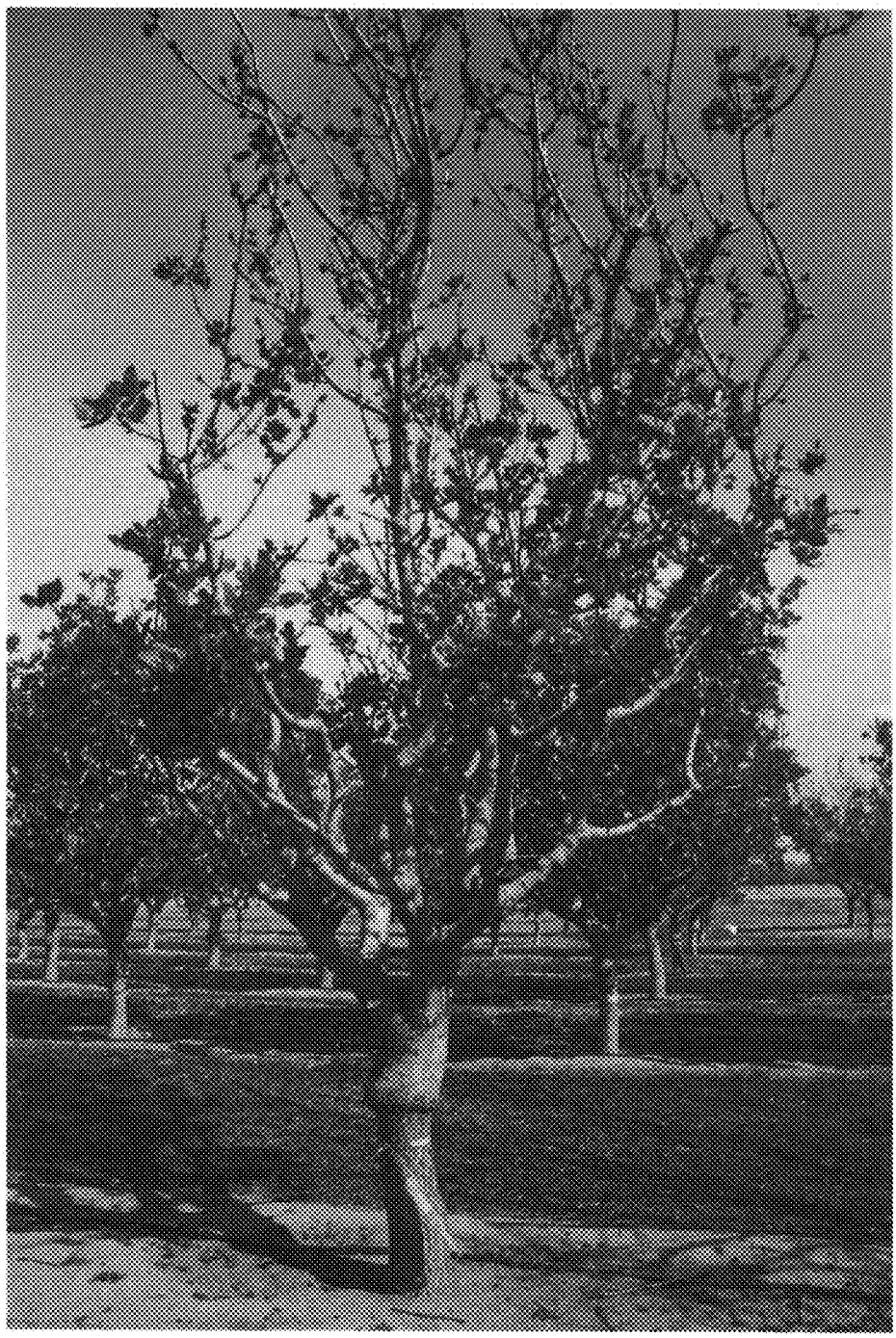
FIG. 1 illustrates a 12-year-old 'Famoso' tree in bloom during Year 25.

The following is a detailed botanical description of the new male pistachio cultivar designated as 'Famoso', including the key differentiating characteristics of this variety and comparisons of certain characteristics of 'Famoso' to other pistachio varieties. Unless otherwise indicated, evaluation data was taken from 12- to 15-year-old trees. Color descriptions are based on the color standards presented in R.H.S. Colour Chart of The Royal Horticultural Society of London (R.H.S.) (1st edition, 1966).

Plant Winter Hardiness, Heat Tolerance, and Drought Tolerance: 'Famoso', as is typical of *Pistacia vera* L., will tolerate temperatures greater than −5° C. to −10° C. The 'UCB-1' rootstock on which it is grafted, however, can sustain significant damage at −5° C. after a few hours. The 'Famoso' cultivar is typically grown in a hot dry environment, and has been grown in a location having typical summer temperatures greater than 40° C. to 42° C. 'Famoso' is similar to 'Kerman' or 'Peters' in that it requires sufficient winter chill to flower (800+ hours below 8° C.). All California pistachio cultivars are grown as an irrigated crop and require about 1000 mm of water during the growing season. Pistachio cultivars will tolerate poor quality water and do not show significant yield loss or damage up to EC (electrical conductivity) 8-12.

Tree Size: Tree height was about 3-4 meters on 15-year-old 'Famoso' trees in Year 28. 'PG1' ('Pioneer Gold 1') rootstock was the particular rootstock used for these particular 'Famoso' trees. Trunk cross sectional areas were taken above and below the graft union and converted to cross sectional area to provide an estimate of tree size at 15 years of age (TABLE 1). 'Randy' (U.S. Plant Pat. No. 18,262) was the standard check cultivar in this plot. Both cultivars were similar in size (not significantly different), with some overgrowth of the scion for 'Famoso'. This has been observed in other cultivars and has not been a problem.

TABLE 1

Trunk cross sectional areas

| Variable | Cultivar | Mean | SE Mean | StDev | p value |
|---|---|---|---|---|---|
| xc top | Famoso | 1.460 | 0.142 | 0.28 | 0.734 |
| | Randy | 1.4016 | 0.084 | 0.168 | |
| xc bottom | Famoso | 0.8432 | 0.0480 | 0.096 | 0.051 |
| | Randy | 1.0229 | 0.0560 | 0.112 | |
| Ratio | Famoso | 1.727 | 0.124 | 0.248 | 0.113 |
| (Top/bottom) | Randy | 1.390 | 0.133 | 0.265 | |

Bark: The bark of 'Famoso' trees is grey (202C-D). Photographs were taken of 15-year-old 'Famoso' and 'Randy' trunks of 2 trees for the purpose of evaluating differences in trunk lenticel density in Year 28. 5 cm and 10 cm templates were used for the photographs. Counts were normalized to counts/cm. 8 to 10 evaluations were done per cultivar with count values of about 50 to 250 counts per observation. ANOVAs were computed with MiniTab 17. No significant differences were found (p=0.329). However, 'Famoso' was observed to have exceptionally irregular and rough lenticels. In most pistachios, lenticels are arranged in horizontal rows, but 'Famoso' lenticels were more random in arrangement and appearance. TABLE 2 shows the mean values for both cultivars (unit is number of lenticels/$cm^2$).

TABLE 2

Mean number of lenticels/$cm^2$

| Cultivar | Mean | SE Mean | StDev | p value |
|---|---|---|---|---|
| Famoso | 18.54 | 1.35 | 4.27 | 0.329 |
| Randy | 16.18 | 2.01 | 5.67 | |

Figure 3A:
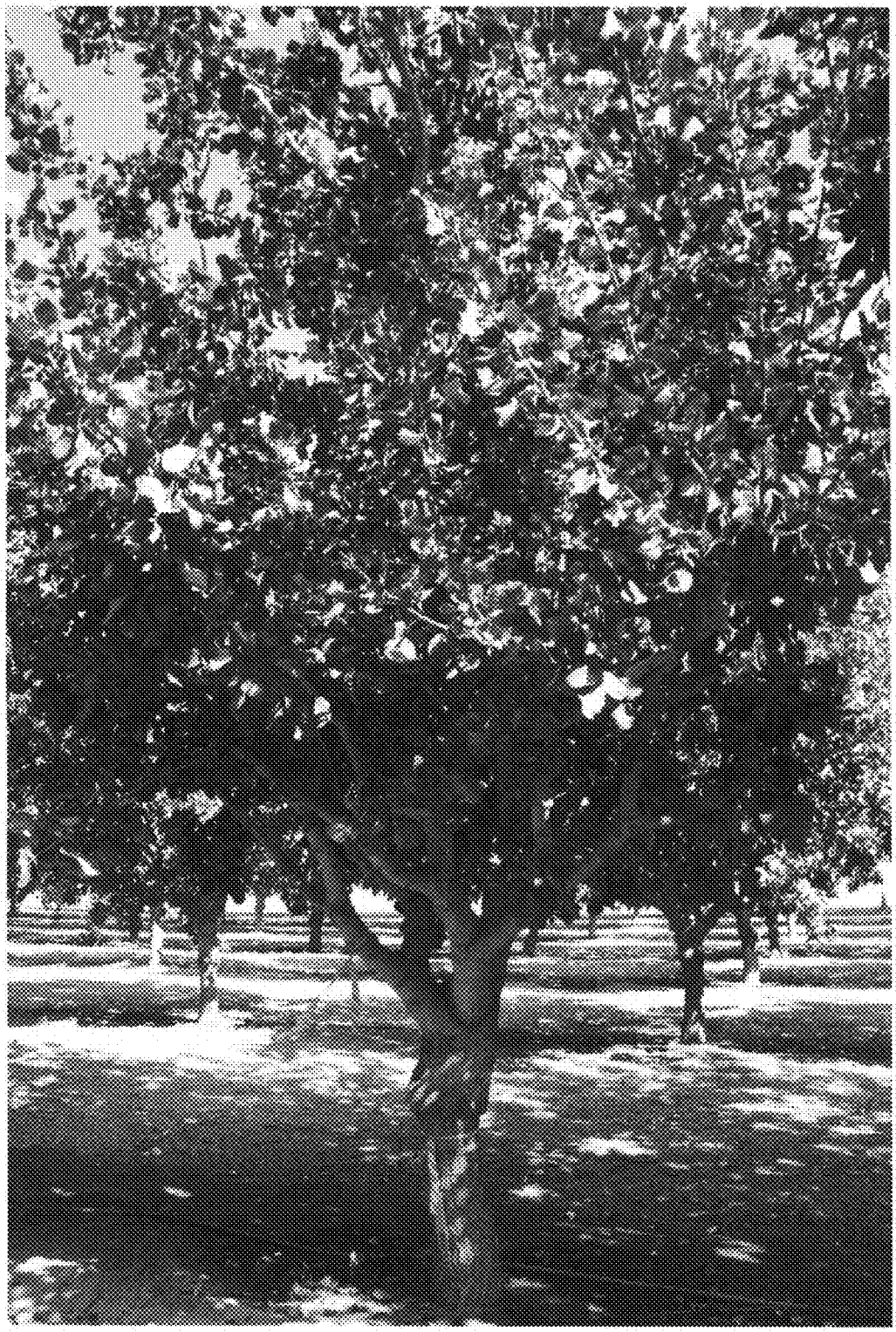
FIG. 3A illustrates the trunk, branches, and canopy of a 12-year-old 'Famoso' tree.
Figure 3B:
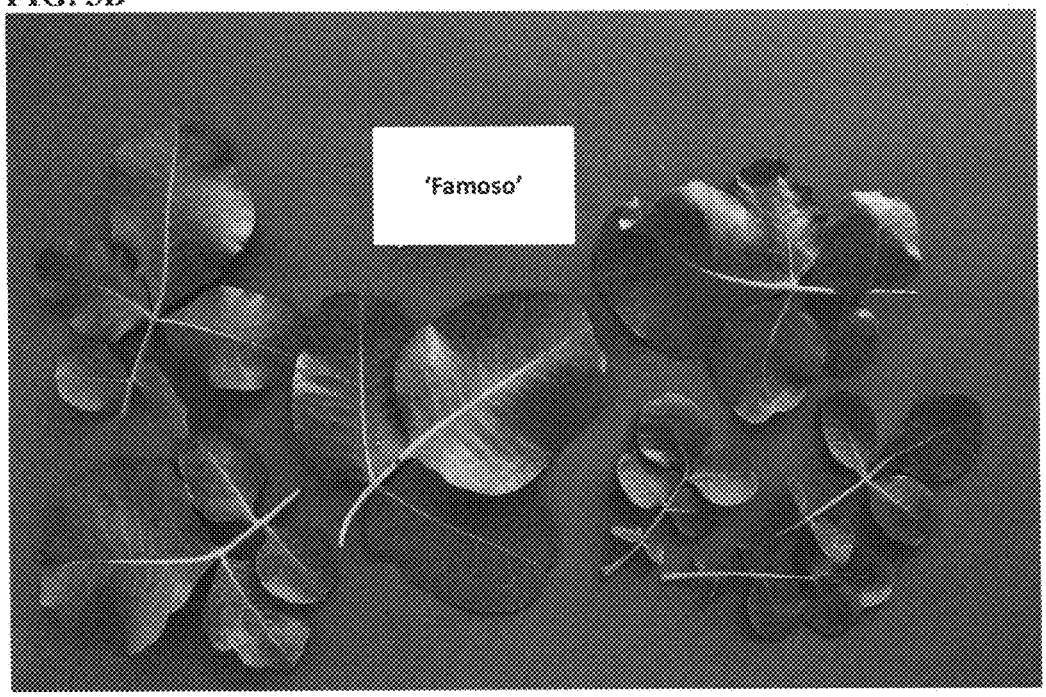
FIG. 3B illustrates the leaves of 'Famoso'.
Figure 3C:
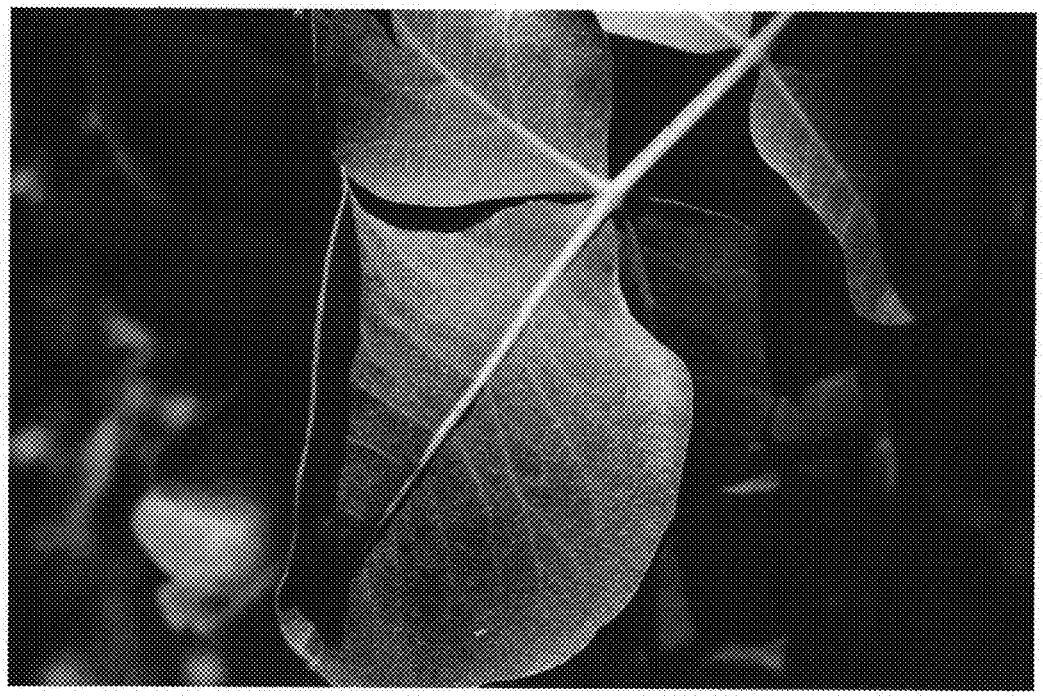
FIG. 3C illustrates the venation pattern on the leaves of a 15-year-old 'Famoso' tree.

Leaves: 'Famoso' leaves are highly variable in the details of their form, shape and size within the tree. In general, the leaves are deciduous simple compound imparipinnate with one or two pairs of oppositely arranged lateral leaflets. However, the leaves can also be trifoliate and on branches with an abundance of new vegetative growth, and only one or no lateral leaflets may be present. Leaflet margins are entire to slightly crenate. Leaflets are oval to ovate and 5-8 cm long. Terminal leaflets can be less than 8 cm to greater than 16 cm. Leaflets vary considerably in shape, in general being ovate and having cuspidate to rounded apex and a rounded base (FIG. 3B). Margins of leaf blades are entire. Leaf surfaces are glabrous, smooth, and waxy. Leaf venation is of the cladodromous type as described by Hickey (1973) Amer. J. Botany 60:17-33, and as shown in FIG. 3C. For leaves, color evaluations were done on at least 3 leaves, each new and mature, collected at random from a 'Famoso' tree during the summer of Year 25 (12-year-old trees). Leaves are shades of green, similar for both upper and lower surfaces. Mature leaves, top surface=137B, bottom surface=137B, 137C, new leaves, top surface=137A, 137B, bottom surface=139C, 138B, leaf midrib=145C. The color of new leaves is 138B to 139C, and the lower surface is 139C. The leaf midrib color for new leaves is 143C. Midrib and petiole colors are the same. Images of the leaves of 'Famoso' are presented in FIG. 3B and FIG. 3C. Typical petiole/leaf values of 15-year-old 'Famoso' trees and 'Randy' trees from Year 28 are shown in TABLE 3 (15 observations). Differences were non-significant at 5% for both petiole and terminal leaflet. The petiole diameter is approximately 1-2 mm, and therefore too small to be measured accurately.

TABLE 3

Typical petiole/leaf values from Year 28

| Cultivar | Variable | Mean | SD | p-value |
|---|---|---|---|---|
| Famoso | petiole length (cm) | 4.99 | 1.32 | 0.322 |
| Randy | petiole length (cm) | 4.57 | 0.88 | |
| Famoso | terminal leaflet (cm) | 11.32 | 1.88 | |
| Randy | terminal leaflet (cm) | 11.11 | 2.34 | |

Flowering Time: 'Famoso' is at full bloom ~1.4 days before or after 'Kerman' and 7-9 days after 'Golden Hills' (U.S. Plant Pat. No. 17,158), but 2-7 days before 'Peters' and ~4 days after 'Randy' (depending on the season). The male pistachio variety 'Famoso' flowered at approximately the same time as the female pistachio variety 'Kerman' over a five year period (TABLE 4A). 'Famoso' trees were 5 years old in Year 18. TABLE 4A shows mean "full bloom" flowering dates for 'Famoso' and 'Randy' over a 5 year period, referenced to 'Kerman' (day 0). Overall, 'Randy' flowered about 4 days before 'Famoso', while 'Famoso' peak flowering was about 1.5 days ahead of 'Kerman'. An image of 'Famoso' in bloom is presented in FIG. 1. An image of a 'Famoso' tree, including images of the trunk, branches, and canopy, is presented in FIG. 3A.

TABLE 4A

Flowering time of 'Famoso' and other varieties relative to 'Kerman'

| | Tejon Ranch | | | | | Little Creek (Famoso) | | | | |
|---|---|---|---|---|---|---|---|---|---|---|
| Date[a] | 4/5, Year 18 | 4/13 Year 19 | 4/21, Year 20 | 4/21, Year 21 | 4/20, Year 22 | 4/1, Year 18 | 4/13, Year 19 | 4/19, Year 20 | 4/16, Year 21 | 4/17, Year 22 |
| | Flowering Date vs. 'Kerman' (female) | | | | | Flowering Date vs. 'Kerman' (female) | | | | |
| 'Kerman' | 0 | 0 | 0 | 0 | 0 | 0 | 0 | 0 | 0 | 0 |
| 'Famoso' | 0 | −2 | −3 | −3 | −2 | −1 | −1 | 0 | −2 | −1 |
| 'Randy' | −4 | −5 | −6 | −7 | −5 | 0 | −9 | −6 | −7 | −4 |
| | Mean Flowering Date vs. 'Kerman' (both locations) | | | | | | | | | |
| 'Kerman' | 0 | | | | | | | | | |
| 'Famoso' | −1.5 | | | | | | | | | |
| 'Randy' | −5.3 | | | | | | | | | |
| | Flower Density Score[b] | | | | | Flower Density Score[b] | | | | |
| 'Famoso' | 3 | 3 | 2 | 3 | 3 | 2 | 3 | 3 | 4 | 3 |
| 'Randy' | 4 | 4 | 4 | 4 | 4 | 3 | 4 | 4 | 4 | 4 |

TABLE 4A-continued

| Flowering time of 'Famoso' and other varieties relative to 'Kerman' | |
|---|---|
| | Mean Flower Density Score (both locations) |
| 'Famoso' | 2.9 |
| 'Randy' | 3.9 |

[a]This is the date that the female variety 'Kerman' flowered in the year identified.
[b]Flower density presented from 1 = low to 4 = high.

Low Chill Flowering: TABLE 4B presents flowering time results for Year 26 (13-year-old 'Famoso' trees), which was a low chill year. In Year 26, 'Famoso' was similar to 'Randy' in terms of flowering date, and 'Famoso' flowered long before 'Peters'. Both 'Randy' and 'Famoso' overlapped with 'Kerman'. Despite the overlap between 'Randy' and 'Kerman' in this low chill year, from TABLE 4A above, it is seen that, in a normal chill year, 'Randy' would flower too early for good pollenization of 'Kerman'. 'Famoso' is intermediate to 'Randy' and 'Peters' for flowering date and thus can overlap with 'Kerman' in both higher and lower chilling seasons.

TABLE 4B

Year 26 flowering evaluation of 'Famoso'. Note mid-bloom (3)/full bloom (4) dates for overlap.

| Cultivar | | Evaluation Date: | | | | | |
|---|---|---|---|---|---|---|---|
| Year 26 | | March 16 | March 19 | March 23 | March 26 | March 30 | April 2 |
| Famoso | Male | 1.9 | 2.3 | 2.6 | 2.7 | 3.3 | 6 |
| Randy | Male | 2 | 2.4 | 2.5 | 2.6 | 3.5 | 6 |
| Peters | Male | 1 | 0.9 | 1 | 1.3 | 2.6 | 2.8 |
| Kerman | Female | 2 | 2.5 | 2.9 | 4.5 | 6 | 6 |
| Golden Hills | Female | 2.4 | 3.2 | 3.5 | 6 | 6 | 6 |
| Lost Hills | Female | 2.4 | 3.2 | 4.2 | 6 | 6 | 6 |

Figure 8:
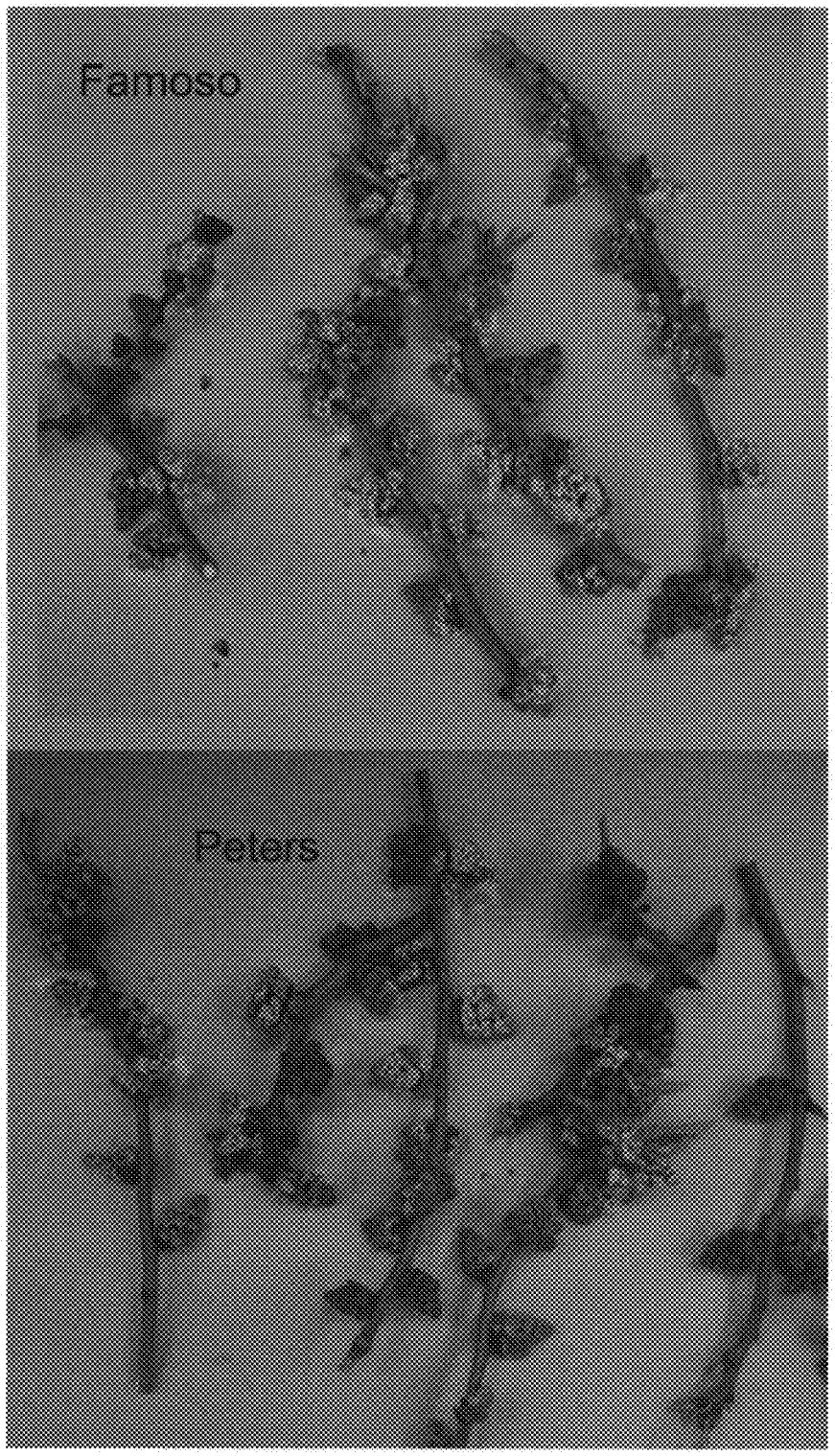
FIG. 8. illustrates a comparison of collected inflorescences from a 15-year-old 'Famoso' tree and a 'Peters' tree showing differences in the colors of the inflorescences.

Bloom ratings 0 to 6:
0 = dormant buds, 1 = green tip on flower bud, 2 => (greater than) 5 open buds on tree, 3 = mid bloom, 4 = full bloom, 5 = late bloom, 6 = bloom finished Flowers and Inflorescences: 'Famoso' inflorescences are borne laterally on branches, rarely as terminal buds. They are located on one year old wood. The flower buds form a branched compound inflorescence as a compact compressed panicle. The panicles are 2 to 5 cm long when fully expanded and shedding pollen with considerable variation in size. Flower development is from base to tip of the panicle and typically spans several weeks, depending on weather conditions during individual seasons. 'Famoso' inflorescences have an orange-reddish (31B to 43A or 43B) appearance, especially on the outer surface, in contrast to 'Peters' inflorescences which are green to light green (136B-139B) with tinges of red (42C-43C) on some predehiscing inflorescences (FIG. 8). Individual flowers are 1-2 mm in diameter. 'Famoso' is a male pistachio tree, which means that all flowers are male. Because there are no female flowers, no seed is produced. Tips and outside of individual flowers are pinkish red (39B-C) changing to yellow (11C, 12D, 13D), and flowers near the base of the panicles are tinged red (42C-43A,B) prior to opening of individual flowers. Flowers do not have petals and have 5-6 stamens each with 4 lobes. Pollen is shed from the terminal ends of the stamens.

Flower Density: On a flower density scale (1=low, 4=high), 'Famoso' ranks at an average of ~3. This is higher than the rating of 'Peters', which ranks at a maximum of 2 as a mature tree. 'Randy' ranks as a strong 4.

Figure 2A:
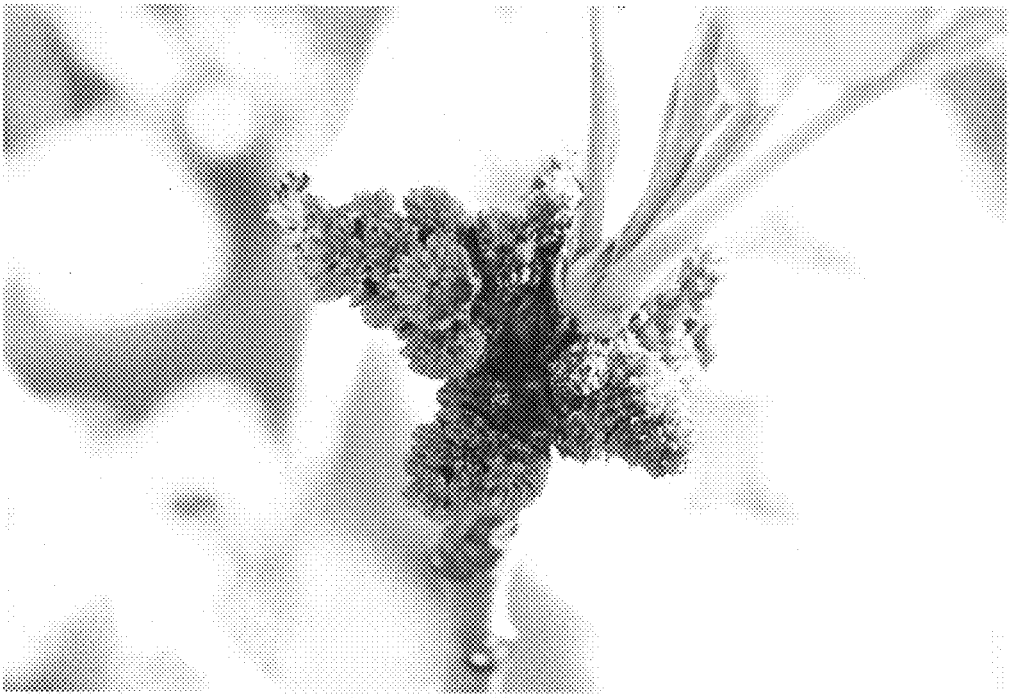
FIG. 2A illustrates flower clusters of a 12-year-old 'Famoso' tree just prior to dehiscence.
Figure 2B:
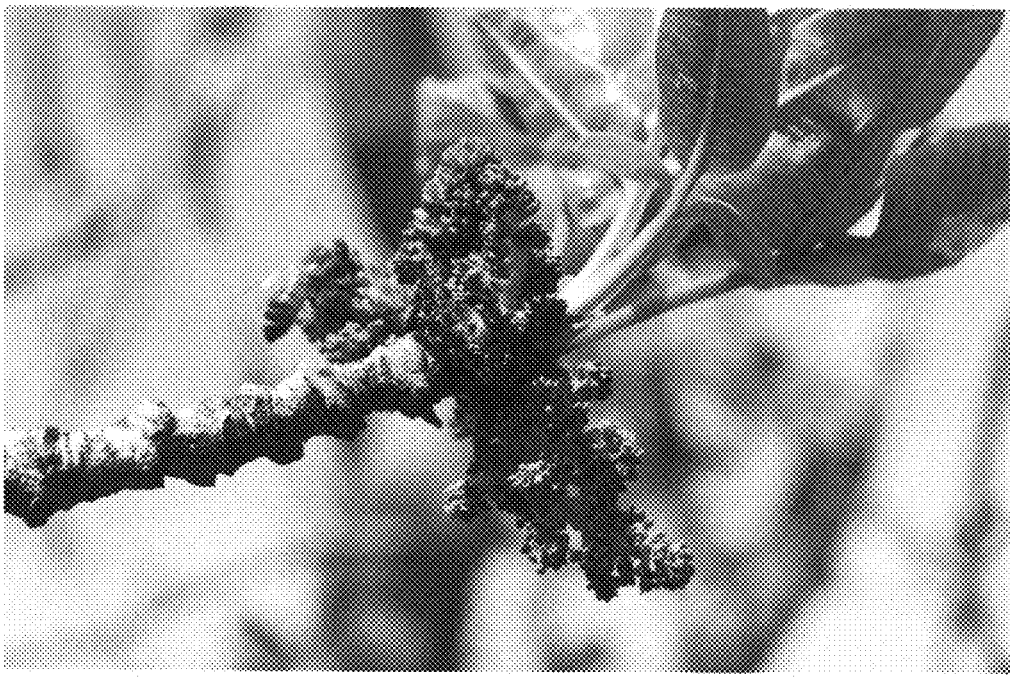
FIG. 2B illustrates flower clusters of a 12-year-old 'Famoso' tree at anther dehiscence.

Pollen: 'Famoso' has good pollen viability, providing good quantities of viable pollen. 'Famoso' sheds a large amount of pollen over a reasonably extended period (19, 14 and 20 days at the Famoso trial in Year 20, Year 21, and Year 22, respectively), and has a highly coincident flowering period with 'Kerman'. 'Famoso' trees were 7 years old in Year 20. Pollen germination at pollen shed for 'Famoso' is high and similar to both 'Randy' and 'Peters'. 'Famoso' produces more abundant flowers and pollen as a juvenile tree compared to 'Peters'. Views of 'Famoso' flower clusters both prior to and at dehiscence are presented in FIG. 2A and FIG. 2B. Pollen counts (germination) for 'Famoso' taken directly after pollen collection in Year 25 (12-year-old trees) was similar to 'Randy' but less than 'Peters' (TABLE 5). 'Famoso' should be a superior pollinizer for 'Kerman' due to better overlap of pollen shed with the 'Kerman' bloom period, especially when the orchard first comes into bearing.

TABLE 5

Pollen counts taken directly after pollen collection in Year 25

| Variety | n | Mean % | Std. dev. % |
|---|---|---|---|
| 'Farnoso' | 8 | 69.711 | 8.796 |
| 'Peters' | 6 | 79.034 | 8.014 |
| 'Randy' | 8 | 67.752 | 7.179 |

Figure 4A:
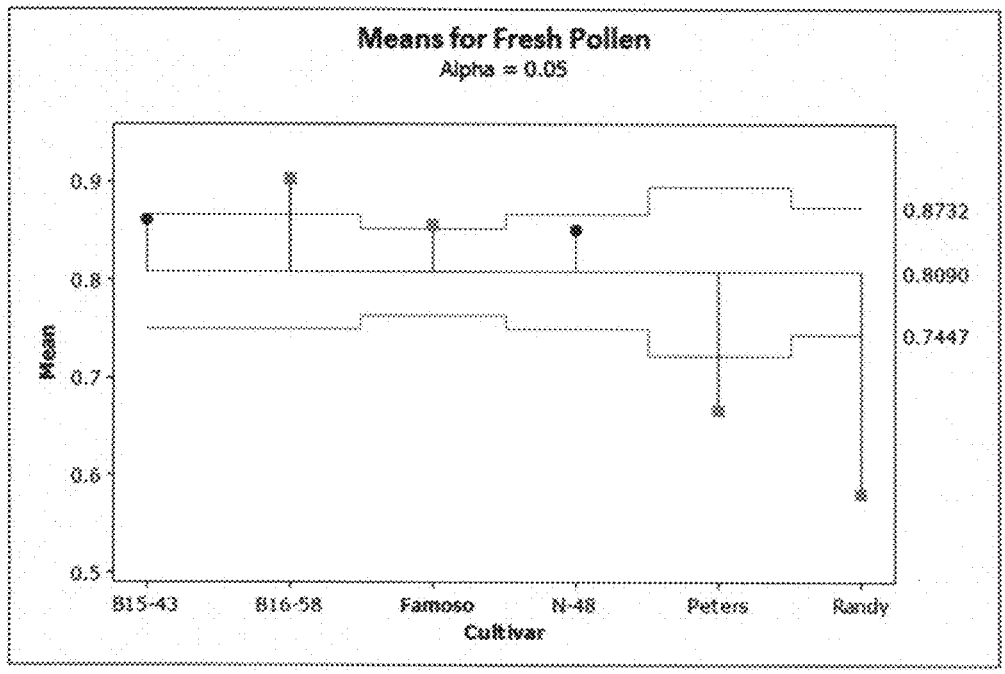
FIG. 4A illustrates the mean germination ratio of freshly-collected pollen for 13-year-old 'Famoso' trees and other male pistachio varieties in Year 26. Shown is the analysis of means (MiniTab 17) with 5% SD, where a value of 1.0=100%.
Figure 4B:
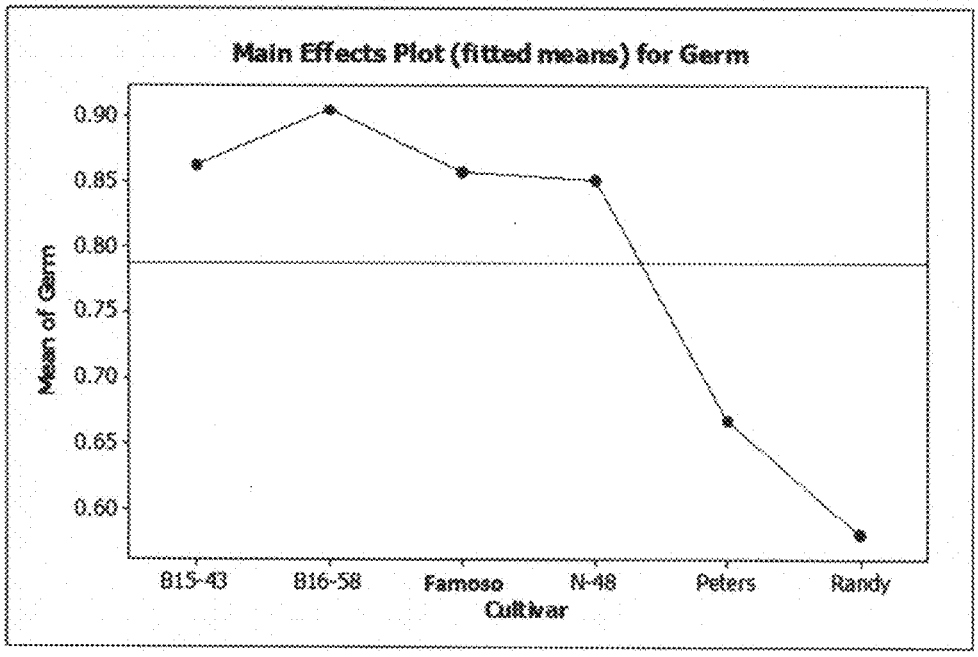
FIG. 4B illustrates a fitted means plot of the germination data presented in FIG. 4A.

Pollen Germination (Year 26): Pollen germination is somewhat a snapshot in time, as it can vary from early to late bloom. Different inflorescences and flowers on the same branch will shed pollen at different times during the bloom period. To analyze fresh pollen counts (germination) in Year 26 (13-year-old 'Famoso' trees), pollen from a variety of male pistachio varieties was collected between March 21 and March 31. Pollen was germinated on 18% sucrose with some boron and calcium nitrate, and at low light in a humid chamber. The pollen of each cultivar was germinated using hanging drop slides. Each slide had two wells and three of these slides were prepared for each cultivar. Germination results are presented below. 'Randy' is a proven pollinizer for the 30,000+ acres of 'Golden Hills' planted in the San Joaquin Valley, and 'Famoso' had higher pollen germination percentages than 'Randy' or 'Peters' in this study (TABLE 6A, TABLE 6B, FIG. 4A, and FIG. 4B).

TABLE 6A

Least Squares Means for germination of fresh pollen in Year 26, counted immediately after flowering.

| Cultivar | Mean % | SE Mean % |
|---|---|---|
| N-48 | 85.09 | 2.334 |
| Peters | 66.67 | 3.301 |
| Randy | 58.09 | 2.557 |
| B15-43 | 86.19 | 2.334 |
| B16-58 | 90.40 | 2.334 |
| Famoso | 85.66 | 1.906 |

TABLE 6B

GLM ANOVA showing highly significant differences among cultivars.
GLM Analysis of Variance for Germination of Fresh Pollen

| Source | DF | SS | MS | F | P |
|---|---|---|---|---|---|
| Cultivar | 5 | 0.84564 | 0.16913 | 25.87 | 0.000 |
| Error | 64 | 0.41841 | 0.00654 | | |
| Total | 69 | 1.26405 | | | |

S = 0.0808560 R-Sq = 66.90% R-Sq(adj) = 64.31%

Figure 5A:
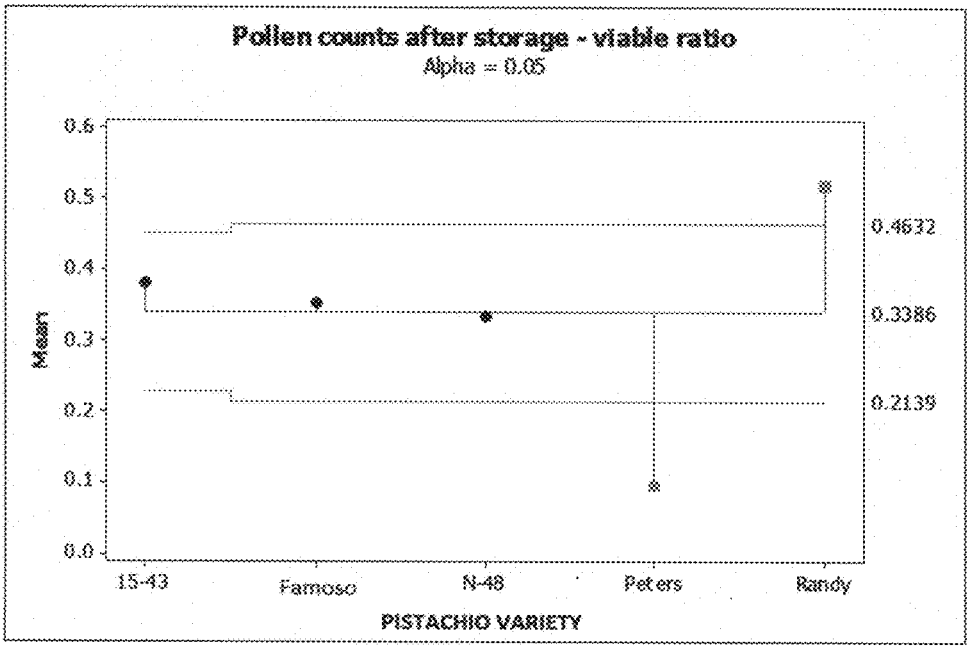
FIG. 5A illustrates the mean germination ratio of stored pollen for 13-year-old 'Famoso' trees and other male pistachio varieties in Year 26. Shown is the analysis of means (MiniTab 17) with 5% SD, where a value of 1.0=100%.
Figure 5B:
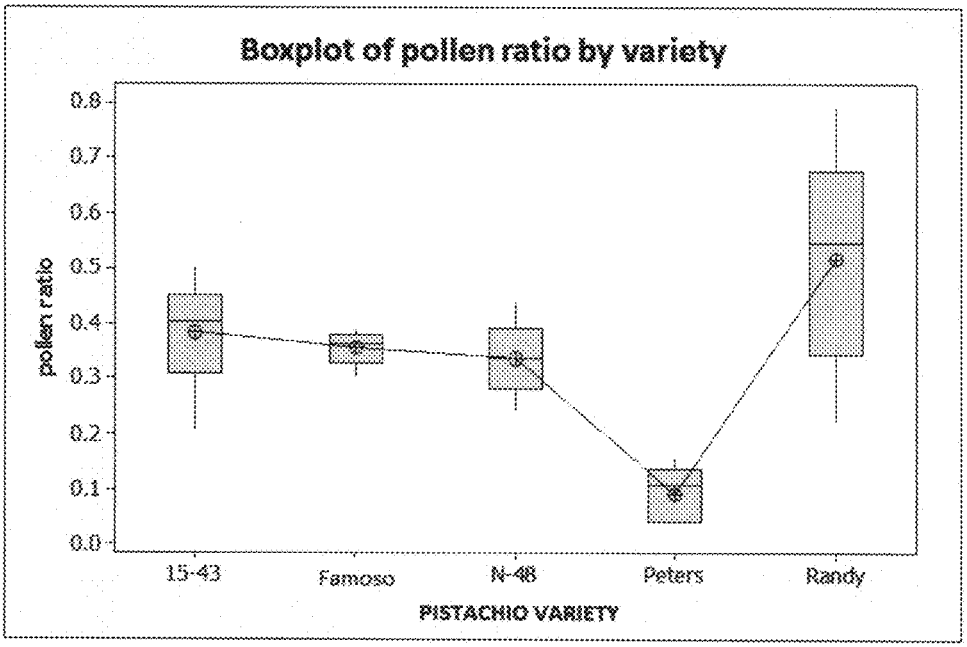
FIG. 5B illustrates boxplots of viable pollen ratios by variety.

Aged Pollen Germination: In Year 26 (13-year-old 'Famoso' trees), pollen was collected from 'Famoso' and several comparison male pistachio varieties, including 'Randy' and 'Peters'. The collected pollen was stored in a refrigerator for two days prior to conducting viable pollen counts (germination assay). This "aged pollen" count provides an estimate of pollen durability. Mean viable pollen counts for each variety are presented in FIG. 5A, and boxplots of these viable pollen ratios by variety are shown in FIG. 5B. Raw mean data and standard errors are presented in TABLE 7. Additional data and analysis are provided in TABLE 8A and TABLE 8B- . Aged pollen for 'Famoso' was more viable than that of 'Peters', but less than that of 'Randy'.

TABLE 7

"Aged Pollen" Viability Ratios

| Variety | Mean | Standard Error Mean |
|---|---|---|
| '15-43' | 0.38198 | 0.04487 |
| 'Famoso' | 0.35480 | 0.04915 |
| 'N-48' | 0.33600 | 0.04915 |
| 'Peters' | 0.09402 | 0.04915 |
| 'Randy' | 0.51728 | 0.04915 |

TABLE 8A

Least Squares Means for germination of pollen in Year 26, counted after 4° C. storage.

| Cultivar | Mean % | SE Mean % |
|---|---|---|
| N-48 | 33.60 | 4.915 |

TABLE 8A-continued

Least Squares Means for germination of pollen in Year 26, counted after 4° C. storage.

| Cultivar | Mean % | SE Mean % |
|---|---|---|
| Peters | 9.40 | 4.915 |
| Randy | 51.73 | 4.915 |
| B15-43 | 38.20 | 4.487 |
| Famoso | 35.48 | 4.915 |

TABLE 8B

GLM ANOVA showing highly significant differences among cultivars.
GLM Analysis of Variance for Germination of Stored Pollen

| Source | DF | SS | MS | F | P |
|---|---|---|---|---|---|
| ACC | 4 | 0.47137 | 0.11784 | 9.76 | 0.000 |
| Error | 21 | 0.25368 | 0.01208 | | |
| Total | 25 | 0.72504 | | | |

S = 0.109908
R-Sq = 65.01%
R-Sq(adj) = 58.35%

Figure 6A:
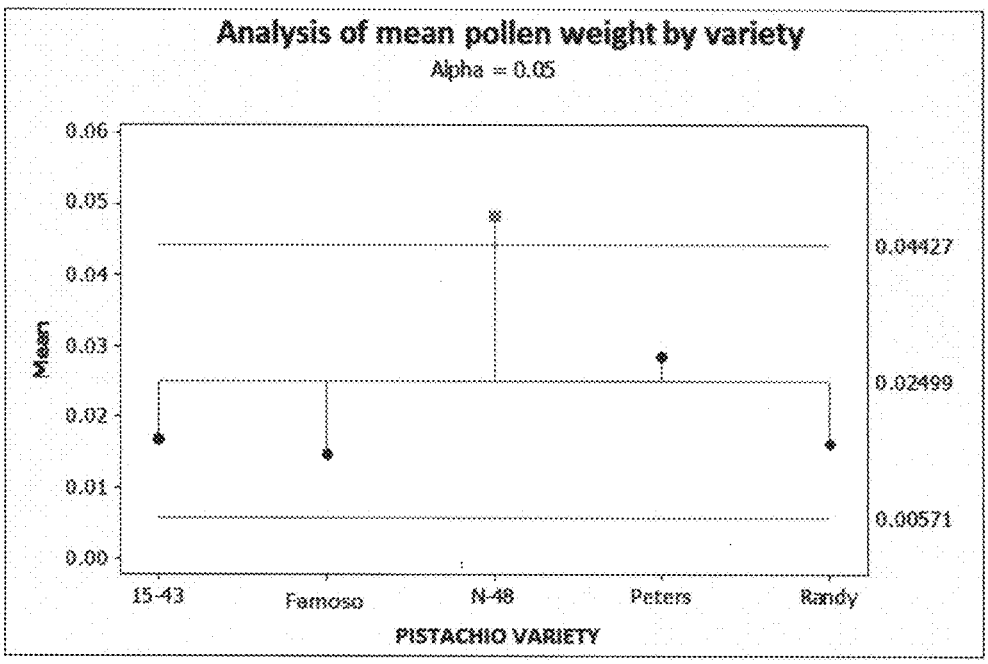
FIG. 6A illustrates the mean pollen weight per inflorescence (grams) for 13-year-old 'Famoso' trees and other male pistachio varieties in Year 26. Shown is the analysis of means (MiniTab 17) with 5% SD.
Figure 6B:
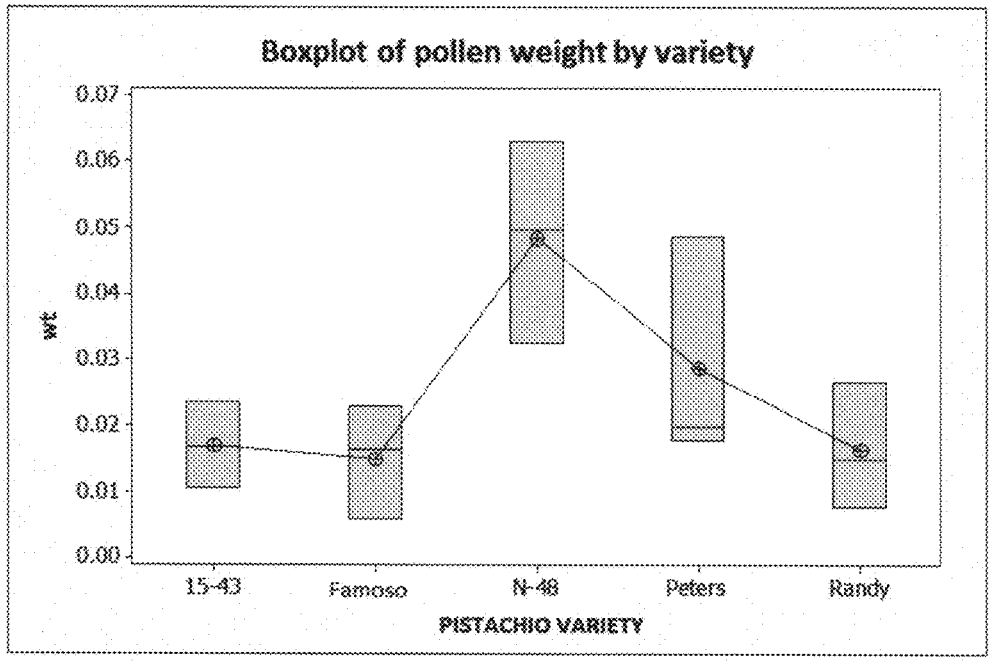
FIG. 6B illustrates boxplots of pollen weight by variety.

Pollen Quantities: During March of Year 26 (13-year-old 'Famoso' trees), branches with dehiscing inflorescences were collected and evaluated. Treatments involved taking four to five shoots that were 8-12 inches long with dehiscing inflorescences and placing them on craft paper overnight, followed by pollen collection the following morning. Pollen from three replicates of each treatment were collected and weighed. Treatments were normalized by counting the number of actively dehiscing inflorescences. ANOVA and ANOM were performed with MiniTab 17. Mean pollen weights for each variety are presented in FIG. 6A, and boxplots of these viable pollen ratios by variety are shown in FIG. 6B. Raw mean data and standard deviations are presented in TABLE 9. Additional data and analysis are provided in TABLE 10A and TABLE 10B. 'Famoso' provides good quantities of viable pollen. Note that variety '15-43' is also referred to as variety 'B15-43'.

TABLE 9

Pollen quantity (weight) in Year 26

| Variety | N | Mean | Standard Deviation |
|---|---|---|---|
| '15-43' | 3 | 0.01683 | 0.00655 |
| 'Famoso' | 3 | 0.01487 | 0.00858 |
| 'N-48' | 3 | 0.04833 | 0.01524 |
| 'Peters' | 3 | 0.02863 | 0.01741 |
| 'Randy' | 3 | 0.01627 | 0.00958 |

TABLE 10A

Least Squares Means for pollen quantities (grams/inflorescence).

| Accession | Mean | SE Mean |
|---|---|---|
| N-48 | 0.04833 | 0.007042 |
| Peters | 0.02863 | 0.007042 |
| Randy | 0.01627 | 0.007042 |
| 15-43 | 0.01683 | 0.007042 |
| Famoso | 0.01487 | 0.007042 |

TABLE 10B

GLM ANOVA for pollen quantities per inflorescence.
GLM for pollen quantification

| Source | DF | SS | MS | F | P |
|---|---|---|---|---|---|
| Acc | 4 | 0.002410 | 0.000602 | 4.05 | 0.033 |
| Error | 10 | 0.001488 | 0.000149 | | |
| Total | 14 | 0.003898 | | | |

S = 0.01220
R-Sq = 61.83%
R-Sq(adj) = 46.56%

Figure 7A:
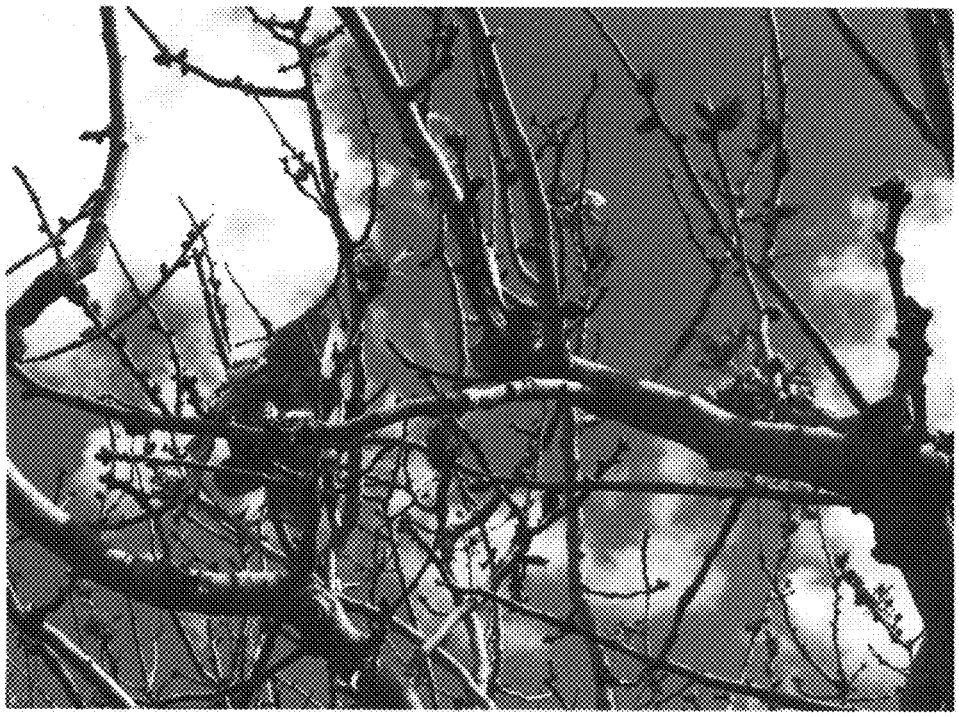
FIG. 7A-FIG. 7B illustrates a comparison of inflorescence density for 13-year-old 'Famoso' trees (FIG. 7A) and 'Peters' (FIG. 7B).
Figure 7B:
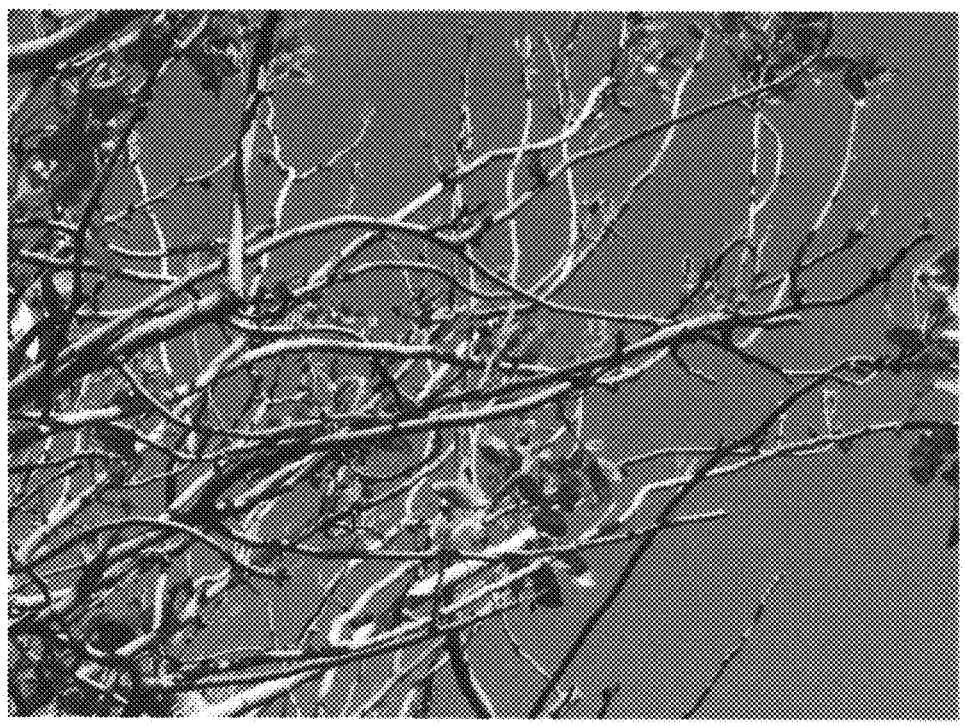

Inflorescence Density: The tree canopies of several male cultivars were photographed to provide an approximate evaluation of the number of inflorescences in the canopy. It is difficult to develop methods that accurately quantify this variable, which is highly dependent on tree size, pruning, and tree health. FIG. 7A and FIG. 7B provide a visual comparison of 'Famoso' and 'Peters', taken at their respective bloom periods. 'Peters' had very scattered bloom in Year 26, with many buds never breaking dormancy.

Response to Pests and/or Diseases: 'Famoso' has not been specifically evaluated for resistance or susceptibility to pistachio diseases. This variety is grown in a location where typical pistachio diseases are minimal, and which is managed to minimize disease development. It is expected that susceptibility to *Botryosphaeria dothidea, Botrytis cinerea,* or *Alternaria alternata* would be similar to other commercial pistachio cultivars since *Pistacia vera* L. in California is generally susceptible to these diseases. Most pistachio insect pests are controlled with insecticides, which have been used where 'Famoso' is grown. Significant differences in unspecified insect damage were not found among the tested cultivars, including 'Famoso'. The flowering date of 'Famoso' is similar to that of 'Peters', and therefore the incidence of *Botryosphaeria dothidea* and *Botrytis cinerea* would be expected to be similar as well.

What is claimed is:

1. A new and distinct variety of pistachio tree designated 'Famoso' as shown and described herein.

* * * * *